United States Patent
Kaizik et al.

(10) Patent No.: US 7,138,552 B2
(45) Date of Patent: Nov. 21, 2006

(54) METHOD FOR PRODUCING $C_{13}$-ALCOHOL MIXTURES

(75) Inventors: Alfred Kaizik, Marl (DE); Walter Tötsch, Marl (DE); Wilhelm Droste, Marl (DE); Wilfried Büschken, Haltern am See (DE); Dirk Röttger, Recklinghausen (DE); Klaus-Diether Wiese, Haltern am See (DE)

(73) Assignee: OXENO Olefinchemie GmbH, Tokyo (JP)

( * ) Notice: Subject to any disclaimer, the term of this patent is extended or adjusted under 35 U.S.C. 154(b) by 160 days.

(21) Appl. No.: 10/513,360

(22) PCT Filed: Mar. 25, 2003

(86) PCT No.: PCT/EP03/03066

§ 371 (c)(1),
(2), (4) Date: Apr. 20, 2005

(87) PCT Pub. No.: WO03/095402

PCT Pub. Date: Nov. 20, 2003

(65) Prior Publication Data

US 2005/0234270 A1    Oct. 20, 2005

(30) Foreign Application Priority Data

May 10, 2002 (DE) .................................. 102 20 799

(51) Int. Cl.
*C07C 29/141* (2006.01)
*C07C 29/16* (2006.01)
*C07C 29/14* (2006.01)

(52) U.S. Cl. ...................... 568/883; 568/882; 568/909; 568/914; 568/913; 568/861; 568/862; 568/863; 568/878; 568/876; 568/880; 568/881; 568/884; 568/885

(58) Field of Classification Search ................ 568/909, 568/914, 913, 861, 862, 863, 883, 878, 876, 568/880, 881, 882, 884, 865

See application file for complete search history.

(56) References Cited

FOREIGN PATENT DOCUMENTS

| DE | 199 55 593 | 5/2001 |
|---|---|---|
| EP | 0 402 051 | 12/1990 |
| EP | 0 987 241 | 3/2000 |
| WO | 01 96508 | 12/2001 |

*Primary Examiner*—Elvis O. Price
(74) *Attorney, Agent, or Firm*—Oblon, Spivak, McClelland, Maier & Neustadt, P.C

(57) ABSTRACT

The present invention relates to a process for preparing a $C_{13}$-alcohol mixture which is suitable, in particular, as precursor for the preparation of compounds having surfactant properties and of plasticizers.

14 Claims, No Drawings

METHOD FOR PRODUCING $C_{13}$-ALCOHOL MIXTURES

This application is a national stage application of International Patent Application No. PCT/EP03/03066, filed on Mar., 25, 2003, and claims priority to German Patent Application No. 102 20 799.2, filed on May 10, 2002, both of which are incorporated herein by reference in their entireties.

The present invention relates to a process for preparing a $C_{13}$-alcohol mixture which is suitable, in particular, as precursor for the preparation of compounds having surfactant properties and of plasticizers.

Alcohols having from about 8 to 20 carbon atoms are precursors for the preparation of nonionic and anionic surfactants. To prepare surfactants, the alcohols are functionalized, for example alkoxylated or glycosidated. The alkoxylates obtained, for example, can either be used directly as nonionic surface-active substances or can be converted into anionic surface-active substances by further functionalization, for example by sulfation or phosphation. The use properties of these surfactants, e.g. their wetting behavior, foam formation, fat solvent capability, biodegradability, etc., are determined by, inter alia, the chain length and the degree of branching of the hydrophobic hydrocarbon radical of the alcohol used. Alcohols which are suitable for the preparation of surfactants are often referred to as surfactant alcohols.

Surfactant alcohols can be obtained by hydrogenation of pure fatty acids, of mixtures of fatty acids, esters of fatty acids and mixtures thereof. These fatty alcohols are linear and have mostly an even number of carbon atoms and from 12 to 18 carbon atoms. Disadvantages of the production of surfactants based on fatty alcohols is that the latter are usually not available as pure substances but only as mixtures of fatty alcohols having different numbers of carbon atoms, their high price and the fact that they are not always available in a sufficient amount.

Surfactant alcohols can also be obtained from ethylene by the Alfol process, which forms an aluminum salt as coproduct.

A further way of preparing surfactant alcohols is to hydroformylate suitable olefins and hydrogenate the resulting aldehydes. The olefins or olefin mixtures used for this purpose determine, inter alia, the linearity of the alcohols and can be produced in various ways.

Olefins which can be used for preparing surfactant alcohols can be prepared from paraffins by chlorination and subsequent dehydrochlorination. These olefins have the disadvantages that they contain chlorine compounds which could interfere in the further synthesis and that chlorine-free end products cannot be guaranteed.

Olefins for the preparation of surfactant alcohols can likewise be obtained by oligomerization of ethylene. One process for preparing olefins having particular chain lengths from ethylene is the SHOP process (Shell Higher Olefins Process). A disadvantage of the processes based on ethylene for obtaining olefins suitable for the preparation of surfactant alcohols is the high price of ethylene.

Olefins which are suitable for the preparation of surfactant alcohols can also be obtained by oligomerization of $C_3$–$C_6$-olefins, in particular propene or butene or mixtures thereof. There are various industrial processes for this purpose.

The oligomerization of lower olefins over acid catalysts, e.g. phosphoric acid on supports or acidic zeolites, gives highly branched oligomers. Oligomerization over specific nickel catalysts gives less branched products. In the Dimersol process (cf. Revue de l'Institut Français du Pétrole, Vol. 37, No. 5, September/October 1982, p. 639 ff), $C_3$- or $C_4$-olefins are oligomerize homogeneously dissolved in the reaction mixture. Typical catalyst systems are nickel(0) complexes in combination with Lewis acids such as $AlCl_3$, $BF_3$, $SbF_5$, etc., or Ni(II) complexes in combination with alkylaluminum halides. A disadvantage of these homogeneously catalyzed processes is the difficulty of separating the catalyst from the reaction mixture. A further disadvantage is that the higher olefins obtained are contaminated with at least traces of halogen which originate from the oligomerization catalyst and cannot be removed completely together with the catalyst. These traces of halogen can adversely affect the subsequent reaction steps and halogen-free end products are not obtained.

Oligomerization over specific heterogeneous supported nickel catalysts, for example in the Octol process of Oxeno GmbH, gives less branched products than the Dimersol process and has the advantage that catalyst-free and halogen-free products are formed (cf. J. Schulze, M. Homann, $C_4$-Hydrocarbons and Derivatives, Springer-Verlag 1989, page 71).

The preparation of $C_{13}$-alcohols by hydroformylation of $C_{12}$-olefins and subsequent hydrogenation of the resulting aldehydes is known.

DE 199 55 593 discloses a process for preparing $C_{13}$-alcohol mixtures, in which $C_{12}$-olefins are hydroformylated in the presence of a cobalt catalyst and the resulting aldehydes are hydrogenated. A yield is not disclosed. DE 199 39 491 A1 (Example 2) describes the preparation of a $C_{13}$-alcohol mixture by hydroformylation of a butene trimer mixture in the presence of a cobalt catalyst and subsequent hydrogenation of the hydroformylation product. The yield of $C_{13}$-alcohol mixture is only 80.4%, based on the $C_{12}$-olefin mixture.

Hydroformylations using rhodium are, with the exception of short-chain olefins such as propene and butenes, carried out industrially only for $C_8$-olefin isomer mixtures (dibutene), cf. Cornils et al., "Applied Homogeneous Catalysis with Organometallic Compounds", Vol. 1, VCH Verlag Weinheim, 1996, p. 35, p. 61 ff. A detailed description of the hydroformylation of $C_8$-olefins is published in DE 33 38 340 and EP 0 272 608. Longer-chain, branched olefins are preferably not hydroformylated using rhodium but are instead hydroformylated with the aid of cobalt catalyst, which is attributable to the lack of activity and selectivity of the rhodium catalyst (Cornils et al. p. 64).

Preferred products of hydroformylation reactions are generally the linear, terminal aldehydes. This is of particular importance when the product of hydrogenation of the aldehyde, namely the alcohol, is used as surfactant.

Since in the case of $C_{12}$-olefins the double bond is frequently internal due entirely to random double bond formation or branched $C_{12}$-olefins are usually formed due to the production process by means of butene trimerization, the preparation of $C_{13}$-alcohols is advantageously carried out by means of a hydroformylation process in which the degree of branching of the aldehydes or alcohols obtained is not increased further. According to Falbe et al. "New Syntheses with Carbon Monoxide", Springer-Verlag Berlin, 1980, p. 38 ff, p. 99, this has been achieved by use of unmodified rhodium instead of cobalt as catalyst. Accordingly, an unmodified cobalt catalyst is used in DE 199 55 593.

It has surprisingly been found that the hydroformylation of $C_{12}$-olefins can be carried out using modified rhodium catalysts; thus, even higher selectivities and yields combined with comparable linearities compared to the corresponding cobalt-catalyzed process were obtained.

The alcohols prepared according to the invention (if appropriate after hydrogenation of the aldehydes) are well suited to the preparation of surfactants and plasticizers.

The invention accordingly provides a process for preparing a $C_{13}$-alcohol mixture by
  a) oligomerization of a butene-containing hydrocarbon mixture over a supported nickel catalyst,
  b) separation of the $C_{12}$-olefin fraction from the reaction mixture,
  c) hydroformylation of the $C_{12}$-olefins,
  d) separation of the catalyst from the hydroformylation mixture and
  e) hydrogenation of the hydroformylation mixture which has been freed of catalyst to give the $C_{13}$-alcohol mixture, wherein the hydroformylation of the $C_{12}$-olefin fraction c) is carried out in the presence of a modified rhodium catalyst.

Unmodified rhodium catalysts have only carbon monoxide (present due to the hydroformylation process) as ligands. The use of these catalysts is not the subject matter of the invention, but purely the use of modified rhodium catalysts. These have co-ordinating ligands, e.g. phosphonites, phosphines or phosphinites.

Starting Materials

In step a) of the process of the invention, preference is given to $C_4$ streams which contain no olefins having other numbers of carbon atoms and virtually no multiply unsaturated hydrocarbons. The isobutene content, based on all butenes, is preferably below 5% by mass, in particular below 3% by mass, very particularly preferably below 1% by mass.

Industrial mixtures which can be used are light petroleum fractions from refineries, $C_4$ fractions from FCC plants or steam crackers, mixtures from Fischer-Tropsch syntheses, mixtures from dehydrogenation of butanes, mixtures formed by olefin metathesis or other industrial processes.

$C_4$ mixtures in which the olefins present are essentially linear butenes can be separated off from the product mixtures. For example, mixtures of linear butenes which are suitable for the process of the invention can be obtained from the $C_4$ fraction from the steam cracker. To obtain such mixtures, butadiene is removed in the first step. This is achieved either by extraction or extractive distillation of the butadiene or its selective hydrogenation. In both cases, a virtually butadiene-free $C_4$ fraction, viz. raffinate 1, is obtained. In the second step, isobutene is removed from the $C_4$ stream, e.g. by reaction with methanol to form methyl tert-butyl ether (MTBE). Other possibilities are reaction of the isobutene in the raffinate II with water to form tert-butanol or acid-catalyzed oligomerization of the isobutene to form diisobutene. The now isobutene-free $C_4$ fraction, viz. raffinate II, comprises, as desired, the linear butenes and possibly butanes. If desired, the 1-butene can be separated off by distillation. Both fractions, viz. that comprising 1-butene or that comprising 2-butenes, can be used in the process of the invention.

A further possible way of preparing a suitable starting material is to hydroisomerize raffinate I or a hydrocarbon mixture having a similar composition. This gives, inter alia, a mixture comprising 2-butenes and possibly n-butane. Such a process is described, for example, in DE 101 52 842.6.

Any multiply unsaturated hydrocarbons (butadiene) still present in the feed streams for the oligomerization are brought to concentrations below 10 ppm by mass, in particular 5 ppm by mass, very particularly preferably 1 ppm by mass, by selective hydrogenation. It is advantageous to remove any traces of oxygen-containing compounds such as alcohols, aldehydes, ketones or ethers and/or sulfur-containing compounds which may be present. For this purpose the $C_4$-hydrocarbon stream can be passed over an absorbent, e.g. a molecular sieve, in particular one having a pore diameter of from >0.4 to 0.5 nm. The concentration of oxygen-containing compounds in the $C_4$-hydrocarbon stream is preferably less than 1 ppm by mass, in particular less than 0.5 ppm by mass.

a) Oligomerization

The oligomerization of the butenes is preferably carried out over supported nickel catalysts. As support materials, it is possible to use, for example, silicon dioxide, aluminum oxide, aluminosilicates, zeolites, zirconium oxide or titanium dioxide, if appropriate after sulfation. Particular preference is given to using titanium-free supported nickel catalysts.

There are various possible routes for the preparation of the catalysts. For example, the catalysts can be prepared by coprecipitation of nickel compounds and support material, e.g. aluminum compounds and/or silicon compounds, filtration and heat treatment. A further possible way is to apply nickel compounds to one of the abovementioned support materials, for example by impregnation or spraying, and subsequently to calcine the catalyst precursor. To prepare the catalysts, it is possible to use nickel compounds such as nickel nitrate, nickel sulfate, nickel chloride or their amine complexes.

In the process of the invention, preference is given to using catalysts which formally comprise nickel oxide, aluminum oxide and silicon oxide. These catalysts comprise from 5 to 50% by mass of nickel, in particular from 10 to 30% by mass. The aluminum contents are in the range from 5 to 30% by mass, in particular in the range from 7 to 20% by mass. The proportions by mass of silicon are from 10 to 40%, in particular from 20 to 30%. As additional components, these catalysts may further comprise from 0.1 to 2% by mass of alkali metal oxide, alkaline earth metal oxide, lanthanum oxide or oxides of the rare earths and, if appropriate, shaping aids.

The catalysts are advantageously used in a form in which they offer a low flow resistance, e.g. granules, pellets or shaped bodies such as tablets, cylinders, spheres, extrudates or rings.

The oligomerization can be carried out batchwise or continuously in all reactors which are customarily employed in solid/liquid contact reactions. When using continuously operating flow reactors, use is usually, but not always, made of a fixed bed. If a fixed-bed flow reactor is used, the liquid can flow upward or downward. Downward flow of the liquid is usually preferred. It is also possible to operate the reactor with product recirculation or in a single pass.

To achieve a high butene conversion, the oligomerization is carried out in a plurality of reactors connected in series, preferably with product recirculation. In such a case, the oligomers are firstly separated from the outputs from the reactors and proportions of the remaining materials are recirculated to the inlets of the appropriate reactors.

The number of reactors connected in series is from 1 to 10, preferably from 1 to 4.

Each reactor can be operated adiabatically, polytropically or virtually isothermally, i.e. with a temperature rise of less than 10° C.

The temperatures at which the reactors are operated are in the range from 20 to 200° C., preferably from 70 to 160° C., very particularly preferably from 80 to 120° C.

The reaction can be carried out at a pressure equal to or above the vapor pressure of the hydrocarbon feed mixture at the respective reaction temperature, preferably at a pressure below 40 bar. To avoid vaporization problems in the reactors, the pressure should be from 2 to 4 bar higher than the vapor pressure of the reaction mixture at the maximum temperature in the reactor.

b) Separation of the $C_{12}$-Olefins from the Reaction Mixture

The reaction mixture from the oligomerization comprises unreacted butenes, possibly n-butane and isobutane, and oligomers having a variety of molar masses ($C_8$-olefins, $C_{12}$-olefins, $C_{16}$-olefins, . . . ). The $C_{12}$-olefin fraction is isolated from this mixture in one or more separation steps. Suitable separation apparatuses are the customary apparatuses known to those skilled in the art. They include, for example, distillation columns such as columns containing random packing, columns containing mesh packing or tray columns which may, if desired, be equipped with bubble caps, sieve plates, sieve trays, valves, side offtakes, etc., evaporators such as thin film evaporators, falling film evaporators, wiped film evaporators, Sambay evaporators, etc., and combinations thereof. The $C_{12}$-olefin fraction is preferably separated off by fractional distillation.

c) Hydroformylation

The $C_{12}$-olefin fraction which has been separated off is hydroformylated and subsequently hydrogenated to prepare the $C_{13}$-alcohol mixture according to the invention.

In the process of the invention, the hydroformylation is carried out in the presence of modified rhodium catalysts so as to achieve a high yield of $C_{13}$-aldehydes and/or the corresponding alcohols.

These rhodium catalysts can be introduced into the process in the form of their active complexes, but in industry it is generally simpler to generate the active catalysts in situ from stable, readily storable rhodium compounds. Rhodium compounds which are suitable for this purpose are, for example, rhodium(II) and rhodium(III) salts, such as rhodium(III) chloride, rhodium(III) nitrate, rhodium(III) sulfate, potassium rhodium sulfate, rhodium(II) or rhodium(III) carboxylates, rhodium(II) and rhodium(III) acetate, rhodium (II) octanoate, rhodium(II) nonanoate, rhodium(III) oxide, salts of rhodic(III) acid, triammonium hexachlororhodate (III). Further suitable compounds are rhodium complexes such as dicarbonylrhodium acetylacetonate, acetylacetonatobis(ethylene)rhodium(I). Particularly useful compounds are rhodium acetate, rhodium octanoate and rhodium nonanoate. In the process of the invention, from about 1 to 200 mol, preferably from 1 to 50 mol and very particularly preferably from 1 to 10 mol, of ligand is added per mol of rhodium. Fresh ligand can be introduced into the reaction at any point in time in order to keep the concentration of free ligand constant.

In the process of the invention, the concentration of rhodium in the hydroformylation reactor is 1–100 ppm by mass, in particular 1–50 ppm by mass, very particularly preferably 1–20 ppm by mass, especially 1–10 ppm by mass.

The process of the invention is carried out using ligands which together with rhodium form complexes which also catalyze the hydroformylation of internal and branched olefins.

The ligands are organic compounds containing nitrogen, arsenic, antimony or preferably phosphorus atoms. The ligands can be monodentate or polydentate, and in the case of chiral ligands it is possible to use either the racemate or else one enantiomer or diastereomer. It is likewise possible to use a mixture of two or more different ligands. As phosphorus ligands, particular preference is given to those which form complexes with rhodium which are less stable than those formed by triphenylphosphine, for example phosphine oxides, phosphites, phosphonites and phosphinites. The hydroformylation of the $C_{12}$-olefin fraction is preferably carried out in the presence of rhodium-phosphite, rhodium-phosphinite or rhodium-phosphonite catalysts.

Examples of phosphites which can be used are trimethyl phosphite, triethyl phosphite, tri-n-propyl phosphite, tri-i-propylphosphite, tri-n-butyl phosphite, tri-i-butyl phosphite, tri-t-butyl phosphite, tris(2-ethylhexyl) phosphite, triphenyl phosphite, tris(2-t-butyl-4-methoxyphenyl) phosphite, tris (2-t-butyl-4methoxyphenyl) phosphite, tris(p-cresyl) phosphite. It is also possible to use sterically hindered phosphite ligands as are described, inter alia, in EP 155 508, U.S. Pat. Nos. 4,668,651, 4,748,261, 4,769,498, 4,774,361, 4,835, 299, 4,885,401, 5,059,710, 5,113,022, 5,179,055, 5,260,491, 5,264,616, 5,288,918, 5,360,938, EP 472 071, EP 518 241 and WO 97/20795. Preference is given to using triphenyl phosphites which are substituted by one or two isopropyl and/or tert-butyl groups on each of the phenyl rings, preferably in the ortho position relative to the phosphite ester group. A very particularly preferred ligand is tris(2,4-di-t-butylphenyl) phosphite.

Examples of phosphonites which can be used are methyldiethoxyphosphine, phenyldimethoxyphosphine, phenyldiphenoxyphosphine, 6-phenoxy-6H-dibenz[c,e][1,2]oxaphosphorin and derivatives thereof in which all or some of the hydrogen atoms are replaced by alkyl or aryl radicals or halogen atoms, and ligands as described in the patents WO 9843935, JP 09-268152 and DE 198 10 794 and in the German patent applications DE 199 54 721 and DE 199 54 510.

Customary phosphinite ligands are described, inter alia, in U.S. Pat. No. 5,710,344, WO 95 06627, U.S. Pat. No. 5,360,938, JP 07082281. Examples are diphenyl(phenoxy) phosphine and derivatives thereof in which all or some of the hydrogen atoms are replaced by alkyl or aryl radicals of halogen atoms, diphenyl(methoxy)phosphine, diphenyl (ethoxy)phosphine, etc.

In the process of the invention, the rhodium-catalyzed hydroformylation is carried out at pressures of from 60 to 300 bar, preferably at pressures of from 150 to 270 bar.

The temperatures for the rhodium-catalyzed hydroformylation are in the range from 40° C. to 180° C., preferably from 90° C. to 150° C., in particular from 100 to 130° C.

d) Separation of the Catalyst from the Hydroformylation Mixture

After the hydroformylation, the major part of the synthesis gas is removed by depressurization. Catalyst and products are separated by distillation from the liquid reaction product mixture. The catalyst and any added ligands, stabilizers, etc., remain in the/as distillation residue. During starting up or if only small amounts of high boilers are formed in the process, it can be advantageous to use a high-boiling (having a boiling point higher than the products and starting materials), inert solvent in which the catalyst dissolves. The catalyst dissolved in the high-boiling solvent can then be returned directly to the reactors. It is particularly advantageous to use the high-boiling by-products formed in the process as high-boiling solvent. Other suitable solvents are high-boiling esters such as 2,2,4-trimethylpentane-1,3-diol monoisobutyrate, which is commercially available as Texanol.

Various methods can be employed for separating off the catalyst by distillation in an industrial process. The catalyst solution is preferably separated off by means of falling film evaporators, short path evaporators or thin film evaporators or combinations of these apparatuses. Such a combination can be employed advantageously, for example, to separate off remaining dissolved synthesis gas and also part of the products and starting olefins still present in a first step (for example in a falling film evaporator) and then to separate off the catalyst in a final, second step (for example in a thin film evaporator).

The distillation pressures are in the range from 5 mbar to 1 bar, preferably from 10 mbar to 100 mbar.

The distillation temperatures are from 40 to 180° C., in particular from 80 to 150° C.

If desired, the bottom product can be additionally stabilized with carbon monoxide, as described in DE 100 48 301.1.

Part of the bottom product is discharged to keep the high boiler concentration in the hydroformylation reactor constant. The other part of the bottom product is recirculated to the hydroformylation reactor. Part of the catalyst (rhodium and ligand) is also removed from the process together with the purged stream. These amounts and other rhodium and ligand deficits have to be made up by addition of further amounts to maintain the above-described catalyst concentration in the hydroformylation reactor.

If appropriate, further products can be separated off from the purged stream, for example by distillation.

The rhodium can be recovered from the purged stream by known methods.

The vapors obtained in the concentration stage can be separated by distillation into aldehydes and alcohols, hydrocarbons and other by-products. Olefins can, if appropriate, be recovered from the hydrocarbon fraction and can be returned to the process.

e) Hydrogenation

The hydroformylation mixture which has been freed of the catalyst or the aldehyde-containing fraction obtained after distillation is hydrogenated in a known manner in the gas phase or preferably in the liquid phase by means of a hydrogen-containing gas.

The hydrogenation can be carried out using, for example, nickel, copper/nickel, copper/chromium, copper/chromium/nickel, zinc/chromium or nickel/molybdenum catalysts. The catalysts can be unsupported or the hydrogenation-active substances or their precursors can have been applied to supports, for example silicon dioxide or aluminum oxide.

Preferred catalysts over which the hydroformylation mixtures are hydrogenated comprise 0.3–15% by mass each of copper and nickel and also, as activators, 0.05–3.5% by mass of chromium and advantageously 0.01–1.6% by mass, preferably 0.02–1.2% by mass, of an alkali metal component on a support material, preferably aluminum oxide or silicon oxide. The amounts quoted refer to the catalyst which has not yet been reduced. The alkali metal component is optional.

The catalysts are advantageously used in a form in which they offer a low flow resistance, e.g. in the form of granules, pellets or shaped bodies such as tablets, cylinders, extrudates or rings. They are advantageously activated before use, e.g. by heating in a hydrogen-containing gas stream.

The hydrogenation, preferably a liquid-phase hydrogenation, is carried out in the pressure range 5–200 bar, in particular in the range 5–100 bar, very particularly preferably in the range 15–50 bar. A hydrogenation in the gas phase can also be carried out at lower pressures, with correspondingly high gas volumes. If a plurality of hydrogenation reactors are used, the total pressures in the individual reactors can be identical or different within the abovementioned pressure limits.

The reaction temperatures are in the range from 120 to 220° C., in particular in the range from 140 to 180° C. Examples of such hydrogenations are described in DE 198 42 369 and DE 198 42 370.

The $C_{13}$-alcohol mixture according to the invention can be obtained from the hydrogenated reaction mixture by customary methods known to those skilled in the art, in particular by fractional distillation.

If desired, the $C_{13}$-alcohol mixture can also be fractionated to give a plurality of fractions.

The invention further provides processes for preparing plasticizers and surface-active compounds.

Plasticizers are prepared from the $C_{13}$-alcohol mixture by reaction with carboxylic acids or their anhydrides, in particular dicarboxylic acids or their anhydrides, to form the corresponding esters. The process for preparing plasticizers comprises firstly preparing an alcohol as claimed in the main claim and reacting this alcohol in a further process step f) with phthalic acid, phthalic anhydride, adipic acid, cyclohexanedicarboxylic acid and/or cyclohexanedicarboxylic anhydride to give the corresponding ester.

Processes for preparing surface-active derivatives of the $C_{13}$-alcohol mixture prepared according to the invention comprise one of the following reaction steps:

g) alkoxylation
h) glycosidation
i) sulfation
j) phosphation
k) alkoxylation with subsequent sulfation (process steps g) and i) carried out in succession)
l) alkoxylation with subsequent phosphation (process steps g) and j) carried out in succession).

The reaction of the surfactant alcohols prepared according to the invention with alkylene oxides to form the corresponding alkoxylates and also their sulfation and/or phosphation are described in Kosswig/Stache, "Die Tenside", Carl Hanser Verlag, Munich, Vienna, 1993, Chapters 2.2 and 2.3.

In the alkoxylation of the $C_{13}$-alcohol mixture to form the corresponding alkoxylates, use is made of alkylene oxide or alkylene oxide derivatives and mixtures thereof. Preference is given to using alkylene oxides having from 1 to 18, in particular from 1 to 10, very particularly preferably from 1 to 6, carbon atom(s). Particular mention may be made of ethylene oxide, propylene oxide, butene oxide and mixtures thereof.

The reaction of the $C_{13}$-alcohol mixture with the alkylene oxide(s) is carried out by customary methods known to those skilled in the art and in apparatuses customary for this purpose.

Even from one $C_{13}$-alcohol and one alkylene oxide, it is possible to prepare many derivative mixtures which differ in their mean molar mass and molar mass distribution.

The mean molar mass of the alkoxylates is determined by the molar ratio of $C_{13}$-alcohol mixture to alkylene oxide. Preference is given to preparing alkoxylated $C_{13}$-alcohol mixtures having from 1 to 100, in particular from 1 to 50, very particularly preferably from 1 to 10, alkylene oxide units. The molar mass distribution is dependent on the process employed.

The $C_{13}$-alcohol mixture can be reacted with one alkylene oxide or with two or more different alkylene oxides. In the reaction of the $C_{13}$-alcohol mixture with two or more different alkylene oxides, different product mixtures are formed, even if mean molar mass and molar mass distribution are disregarded. If the $C_{13}$-alcohol mixture is reacted with a mixture of the different alkylene oxides, the more reactive alkylene oxides are added preferentially onto the $C_{13}$-alcohol mixture at the beginning of the reaction, and a more or less random incorporation of the different alkylene oxide groups occurs subsequently.

On the other hand, if the various alkylene oxides are added separately in succession, alkoxylates in which the alkylene oxide units are present in the form of blocks which correspond essentially to the order of addition are formed.

The reaction of $C_{13}$-alcohol mixtures with alkylene oxide(s) can be catalyzed by acids, bases or amphoteric substances. For example, alkali metal hydroxides, alkali metal alkoxides or alkaline earth metal hydroxides can be used as basic catalysts and aluminum trichloride and boron trifluoride can be used as Lewis acids.

Depending on the reactivity of the alkylene oxide(s) used and depending on the process employed, the alkoxylation temperatures are in the range from 70 to 260° C., in particular in the range from 90 to 230° C.

The pressure is preferably in the range from atmospheric pressure to 300 bar. The alkylene oxide used may, if appropriate, be diluted with an inert liquid or with an inert gas.

These alkoxylated derivative mixtures of the $C_{13}$-alcohol mixture are nonionic surfactants having a high surface activity. These mixtures can therefore be used in many fields of application, for example as dispersants, paper auxiliaries, corrosion inhibitors and as auxiliaries for dispersions.

Glycosylated $C_{13}$-alcohol mixtures can be obtained by single, double or multiple reaction of $C_{13}$-alcohol mixtures with monosaccharides, disaccharides or polysaccharides by customary methods known to those skilled in the art.

Here, two different synthetic routes can be employed. In one, the $C_{13}$-alcohol mixture is reacted directly with a saccharide to eliminate water and form the target product. Acids such as hydrochloric acid or sulfuric acid are used as catalyst in this reaction. The reaction usually forms oligosaccharides having a random chain length distribution. In the other synthetic route, the saccharide is firstly converted into a derivative and the intermediate is reacted with the $C_{13}$-alcohol mixture to form the target product. The intermediate can be an acetal obtained by reaction of a saccharide, if appropriate in the form of an aqueous solution, with an alcohol having from 1 to 8 carbon atoms, or can be an O-acetalchlorosaccharide formed in the reaction of a saccharide with hydrogen chloride. Both intermediates give the target products on reaction with $C_{13}$-alcohol mixtures. In the route via the chlorine compound, it is advantageous to add a base to bind the acid liberated.

The glycosidation is preferably carried out using monosaccharides, for example hexoses or pentoses, in particular glucose.

The $C_{13}$-alcohol mixture can be reacted with one saccharide or two or more saccharides. In the reaction of the $C_{13}$-alcohol mixture with two or more different saccharides, different product mixtures can be formed, even if mean molar mass and molar mass distribution are disregarded. If the $C_{13}$-alcohol mixture is reacted with a mixture of different saccharides, the more reactive saccharides add preferentially onto the $C_{13}$-alcohol mixture at the beginning of the reaction, and more or less random incorporation of the different saccharide groups occurs subsequently. On the other hand, if the various saccharides are used separately in succession, glycosylates in which the saccharide units are present in the form of blocks which correspond essentially to the order of addition are formed.

The processes and reaction conditions employed in the glycosidation are described, for example, in Ullmann's Encyclopedia of Industrial Chemistry, $5^{th}$ edition, Vol. A25 (1994), pp. 792–793, and the references cited therein.

The sulfation of the $C_{13}$-alcohol mixture or its alkoxylates to form the corresponding sulfation products (alkyl sulfates or alkyl ether sulfates) is carried out by reaction with sulfuric acid or sulfuric acid derivatives.

U.S. Pat. Nos. 3,462,525, 3,420,875 and 3,524,864 describe processes for the sulfation of alcohols. These processes can be utilized for the sulfation of $C_{13}$-alcohol mixtures or their alkoxylates. Further suitable methods of sulfation are also described in Ullmann's Encyclopedia of Industrial Chemistry, 5th Edition, Vol. A25 (1994), pp. 779–783 and in Kirk-Othmer Encyclopedia of Chemical Technology, 4th Edition, Vol. 23 (1997), pp. 500–502, and the references cited therein.

The sulfation of the $C_{13}$-alcohol mixture prepared according to the invention is preferably carried out using concentrated sulfuric acid. The concentration of the sulfuric acid is preferably from 75 to 100% (by mass), in particular from 85 to 98%.

To achieve high yields, the molar ratio of alcohol to sulfating agent in the esterification of the $C_{13}$-alcohol mixture is preferably from 1/1 to 1/1.5, in particular from 1/1 to 1/1.2.

The sulfation is preferably carried out in a temperature range from ambient temperature 20° C. to 80° C., in particular in the range from 40 to 75° C.

As further suitable sulfating agents, it is possible to use, for example, sulfur trioxide, solutions of sulfur trioxide in sulfuric acid (oleum), chlorosulfonic acid and sulfuryl chloride. If sulfur trioxide is used as sulfating agent, the sulfation can be carried out in a falling film evaporator, preferably in countercurrent.

The subsequent work-up of the sulfation product mixture, e.g. neutralization and removal of any solvents used, is carried out by customary methods known to those skilled in the art.

Phosphation of the $C_{13}$-alcohol mixture or its alkoxylates to form the desired phosphation products (alkyl phosphates or alkyl ether phosphates) is preferably carried out by esterification using phosphoric acid or phosphoric acid derivatives.

The phosphation of the $C_{13}$-alcohol mixture according to the invention and its alkoxylated products is generally carried out in a manner analogous to sulfation.

Suitable methods of phosphating alcohols are known to those skilled in the art and are described, for example, in Kirk-Othmer Encyclopedia of Chemical Technology, $4^{th}$ Edition, Vol. 23 (1997), pp. 504–506, and in R. L. Rudnick et al. "Synthetic Lubricants and High-Performance Functional Fluids" Marcel Dekker New York, 1999, p. 103 ff.

Suitable phosphating agents are, for example, phosphoric acid, polyphosphoric acid, phosphorus pentoxide and phosphoryl chloride.

The invention further provides for the use of the functionalized $C_{13}$-alcohol mixtures prepared according to the invention as surfactants, dispersants, paper auxiliaries, corrosion inhibitors and as auxiliaries for dispersions.

The following examples illustrate the invention without restricting its scope which is defined by the description and the claims.

EXAMPLE 1

Comparative Example

Hydroformylation of $C_{12}$-Olefin (Tributene) in the Presence of a Cobalt Catalyst In a 2 l high-pressure autoclave provided with a stirrer and electric heating, 1000 g of tributene ($C_{12}$-olefin mixture from the Octol process of OXENO GmbH) were hydroformylated at 180° C. and a constant synthesis gas pressure of 270 bar in the presence of a cobalt catalyst. The synthesis gas consisted of 50% by volume of CO and 50% by volume of $H_2$.

To prepare the active cobalt catalyst, an aqueous cobalt acetate solution containing 1.35% by mass of Co was used as catalyst precursor. This cobalt acetate solution was treated with synthesis gas at 170° C. and 280 bar for 5 h while stirring. After cooling to room temperature and depressurization, the cobalt carbonyls formed were transferred into the organic phase by extraction with tributene starting material. After the aqueous phase had been separated off, the tributene laden with cobalt carbonyls and having a cobalt content of 0.09% by mass (calculated as metal) was hydroformylated for 5 hours under the abovementioned reaction conditions. The olefin conversion was monitored both by means of GC analysis and also via the amount of synthesis gas taken up.

After cooling to room temperature, the reaction mixture was depressurized, discharged from the autoclave and freed of the Co catalyst by treatment with 5% strength acetic acid and air at 80° C.

According to GC analysis, the reaction product mixture comprised 22.5% by mass of $C_{12}$-olefin, 23.5% by mass of $C_{13}$-aldehyde (isotridecanal), 44.3% by mass of $C_{13}$-alcohol (isotridecanol) and 9.7% by mass of high boilers. This product composition corresponds to a tributene conversion of 75.4% and a yield of desired product ($C_{13}$-aldehyde/alcohol) of 62.4%.

EXAMPLE 2

According to the Invention

Hydroformylation of $C_{12}$-Olefin (Tributene) in the Presence of a Rhodium Catalyst In a 2 l autoclave, 1000 g of tributene from the Octol process were reacted at 135° C. under a synthesis gas pressure of 270 bar for 5 hours in the presence of a phosphite-modified rhodium catalyst. The active rhodium catalyst was generated in situ from rhodium octanoate and tris(2,4-di-tert-butylphenyl) phosphite.

The rhodium concentration (based on the total mass of the reaction mixture) was set to 10 ppm, and the phosphorus/rhodium molar ratio (P/Rh) was 10:1.

The conversion of the olefin was monitored both by means of GC analysis and via the amount of synthesis gas taken up. After 5 hours, the reaction was stopped. The reaction product mixture comprised 13.1% by mass of $C_{12}$-olefin, 80.9% by mass of $C_{13}$-aldehyde (isotridecanal), 4.6% by mass of $C_{13}$-alcohol (isotridecanol) and 1.4% by mass of high boilers. This product composition corresponds to a tributene conversion of 85.0% and a yield of desired product ($C_{13}$-aldehyde/alcohol) of 83.0%.

Compared to the hydroformylation of the $C_{12}$-olefin isomer mixture in the presence of a cobalt catalyst, as described in Example 1, the rhodium-catalyzed hydroformylation leads to a significant increase in the yield of desired product to 83.0%.

What is claimed is:

1. A process for preparing a $C_{13}$-alcohol mixture by
    a) oligomerization of a butene-containing hydrocarbon mixture over a supported nickel catalyst,
    b) separation of the $C_{12}$-olefin fraction from the reaction mixture,
    c) hydroformylation of the $C_{12}$-olefins,
    d) separation of the catalyst from the hydroformylation mixture and
    e) hydrogenation of the hydroformylation mixture which has been freed of catalyst to give the $C_{13}$-alcohol mixture,
    wherein the hydroformylation of the $C_{12}$-olefin fraction c) is carried out in the presence of a modified rhodium catalyst.

2. The process as claimed in claim 1, wherein the hydroformylation of the $C_{12}$-olefin fraction c) is carried out in the presence of a rhodium-phosphite catalyst.

3. The process as claimed in claim 2, wherein the hydroformylation of the $C_{12}$-olefin fraction c) is carried out in the presence of a catalyst comprising rhodium and tris(2,4-di-t-butylphenyl)phosphite.

4. The process as claimed in claim 1, wherein the hydroformylation of the $C_{12}$-olefin fraction c) is carried out in the presence of a rhodium-phosphonite catalyst.

5. The process as claimed in claim 1, wherein the hydroformylation of the $C_{12}$-olefin fraction c) is carried out in the presence of a rhodium-phosphonite catalyst.

6. The process as claimed in claim 1, wherein the oligomerization of the butene-containing hydrocarbon mixture is carried out over a supported nickel catalyst.

7. The process as claimed in claim 6, wherein the oligomerization of the butene-containing hydrocarbon mixture is carried out over a titanium-free supported nickel catalyst.

8. The process claimed in claim 1, which further comprises:
    reacting the $C_{13}$-alcohol mixture with a compound selected from the group consisting of phthalic acid, phthalic anhydride, adipic acid, cyclohexanedicarboxylic acid, cyclohexanedicarboxylic anhydride, and mixtures thereof to obtain an esterified $C_{13}$-alcohol mixture.

9. The process claimed in claim 1, which further comprises:
    reacting the $C_{13}$- alcohol mixture with a compound selected from the group consisting of ethylene oxide, propylene oxide, butylene oxide, and mixtures thereof to obtain an alkoxylated $C_{13}$-alcohol mixture.

10. The process claimed in claim 1, which further comprises:
    reacting the $C_{13}$-alcohol mixture with a saccharide selected from the group consisting of a monosaccharide, a disaccharide, a polysaccharide, and mixtures thereof to obtain a glycosylate $C_{13}$-alcohol mixture.

11. The process claimed in claim 1, which further comprises:
    reacting the $C_{13}$-alcohol mixture with a compound selected from the group consisting of sulfuric acid, $SO_3$, chlorosulfonic acid, sulfuryl chloride, and mixtures thereof to obtain a sulfonated $C_{13}$-alcohol mixture.

12. The process claimed in claim 1, which further comprises:

reacting the $C_{13}$-alcohol mixture with a compound selected from the group consisting of phosphoric acid, a phosphoric acid derivative, and mixtures thereof to obtain a phosphorylate $C_{13}$-alcohol mixture.

13. The process claimed in claim 1, which further comprises:

reacting the $C_{13}$-alcohol mixture with a compound selected from the group consisting of ethylene oxide, propylene oxide, butylene oxide, and mixtures thereof to obtain an alkoxylated $C_{13}$-alcohol mixture; and reacting the alkoxylated $C_{13}$-alcohol mixture with a compound selected from the group consisting of sulfuric acid, $SO_3$, chlorosulfonic acid, sulfuryl chloride, and mixtures thereof to obtain a sulfonated, alkoxylated $C_{13}$-alcohol mixture.

14. The process claimed in claim 1, which further comprises:

reacting the $C_{13}$-alcohol mixture with a compound selected from the group consisting of ethylene oxide, propylene oxide, butylene oxide, and mixtures thereof to obtain an alkoxylated $C_{13}$-alcohol mixture; and reacting the alkoxylated $C_{13}$-alcohol mixture with a compound selected from the group consisting of phosphoric acid, a phosphoric acid derivative, and mixtures thereof to obtain a phosphorylated, akloxylated $C_{13}$-alcohol mixture.

* * * * *

UNITED STATES PATENT AND TRADEMARK OFFICE
CERTIFICATE OF CORRECTION

PATENT NO. : 7,138,552 B2
APPLICATION NO. : 10/513360
DATED : November 21, 2006
INVENTOR(S) : Kaizik et al.

It is certified that error appears in the above-identified patent and that said Letters Patent is hereby corrected as shown below:

On the title page, Item (73), the Assignee's City and Country is incorrect. Item (73) should read:
-- (73) Assignee: OXENO Olefinchemie GmbH, Marl (DE) --

Signed and Sealed this

Thirteenth Day of February, 2007

JON W. DUDAS
*Director of the United States Patent and Trademark Office*